United States Patent [19]

Brooks et al.

[11] Patent Number: 5,717,480
[45] Date of Patent: Feb. 10, 1998

[54] OPHTHALMIC INSTRUMENT SUPPORT AND LIGHTING SYSTEM

[75] Inventors: David M. Brooks; Robert E. Marconet, both of Cincinnati, Ohio

[73] Assignee: Reliance Medical Products, Inc., Mason, Ohio

[21] Appl. No.: 549,634

[22] Filed: Oct. 27, 1995

[51] Int. Cl.⁶ .................................................. A61B 3/10
[52] U.S. Cl. ..................................... 351/221; 351/200
[58] Field of Search ................................. 351/200, 205, 351/221, 245, 210; 315/360, 363, DIG. 4

[56] References Cited

U.S. PATENT DOCUMENTS

| D. 292,526 | 10/1987 | Nakayama | D24/1.1 |
|---|---|---|---|
| 3,201,795 | 8/1965 | Cüppers et al. | 351/245 |
| 3,304,609 | 2/1967 | Horowitz et al. | 32/22 |
| 3,572,913 | 3/1971 | Korb et al. | 351/245 |
| 3,724,931 | 4/1973 | Nevyas et al. | 351/221 |
| 3,832,041 | 8/1974 | Lieberman | 351/221 |
| 3,944,342 | 3/1976 | Martinez | 351/206 |
| 3,986,030 | 10/1976 | Teltscher | 351/210 X |
| 4,094,593 | 6/1978 | Kutscherauer et al. | 351/245 |
| 4,095,379 | 6/1978 | Weintraub | 52/29 |
| 4,116,548 | 9/1978 | Persson | 351/245 |
| 4,165,924 | 8/1979 | Mohrman | 351/245 |
| 4,166,602 | 9/1979 | Nilsen et al. | 248/280 |
| 4,379,237 | 4/1983 | Mosteller, Jr. | 307/141 |
| 4,421,394 | 12/1983 | Schön et al. | 351/245 |
| 4,536,065 | 8/1985 | Sheingorn | 351/239 |
| 4,580,884 | 4/1986 | Sugiura et al. | 351/245 |
| 4,643,547 | 2/1987 | Collins et al. | 351/245 |
| 4,741,506 | 5/1988 | Schwaegerle | 248/430 |
| 4,790,647 | 12/1988 | Mann et al. | 351/245 |
| 4,852,500 | 8/1989 | Ryburg et al. | 248/918 |
| 4,870,954 | 10/1989 | Satoh | 128/24 A |
| 5,000,563 | 3/1991 | Gisel et al. | 351/245 |
| 5,059,871 | 10/1991 | Pearlman et al. | 315/316 |
| 5,329,431 | 7/1994 | Taylor | 362/85 |

OTHER PUBLICATIONS

Brochure, "905 Ophthalmic Delivery System", Reliance® Medical Products, Inc., 3535 Kings Mills Road, Mason, OH 45040-2303, ©1993.
Brochure, "PERC™ Programmable Electronic Room Controller", Marco Ophthalmic, Inc., Jan., 1995.

*Primary Examiner*—Huy Mai
*Attorney, Agent, or Firm*—Wood, Herron & Evans, L.L.P.

[57] ABSTRACT

The present invention provides a uniquely position adjustable ophthalmic instrument support table for use in conjunction with an examining chair and a lighting system which allows the user to program the desired room lighting independently for each of several inputs such as instrument switches, examination lights or other electrical devices used during an ophthalmic examination. The ophthalmic instrument support table includes a base unit and a table top mounted to the base unit by support structure allowing four degrees of freedom to adjust the location of the table top with respect to both the patient seated in the chair and the doctor examining the patient on the opposite side of the table. The lighting control system allows one or two circuits of room lights to be adjusted in intensity and to have this adjustment automatically recalled to set the programmed room lighting condition upon activation of the input.

16 Claims, 12 Drawing Sheets

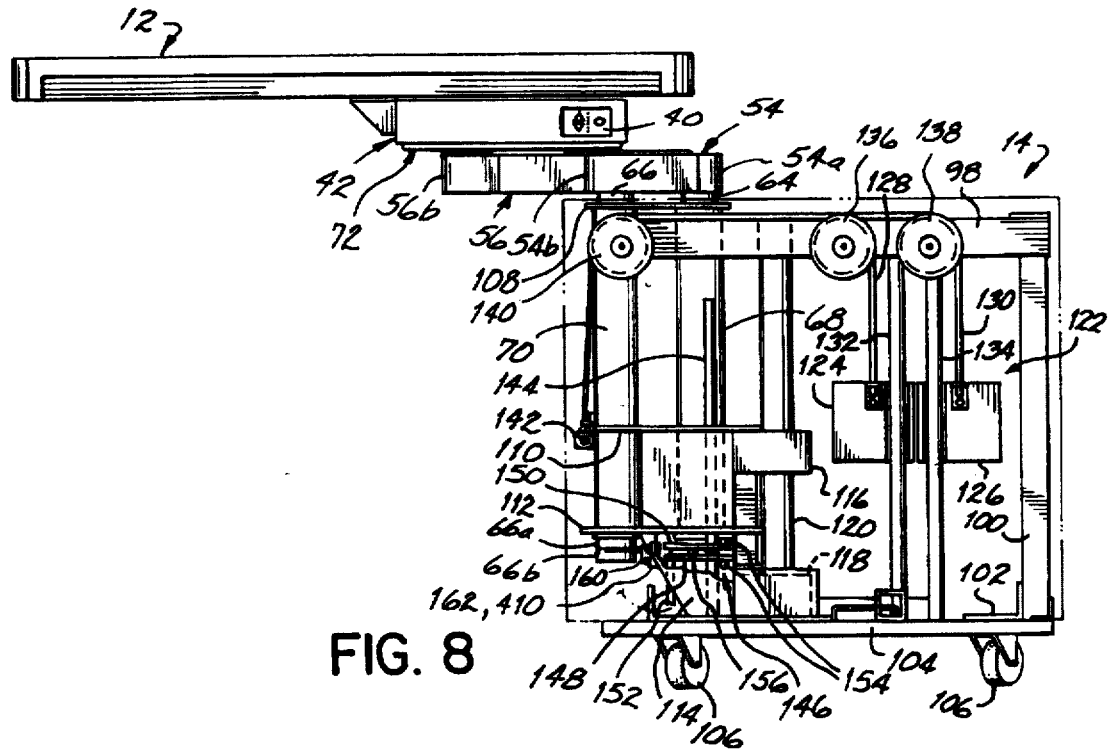
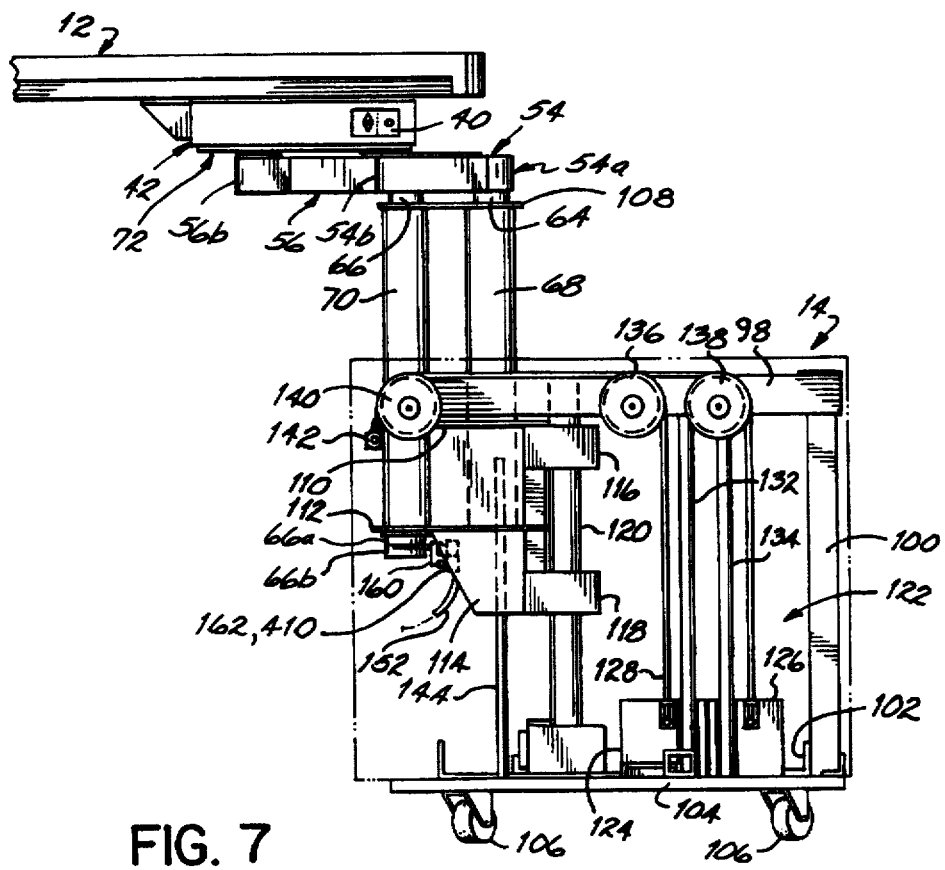

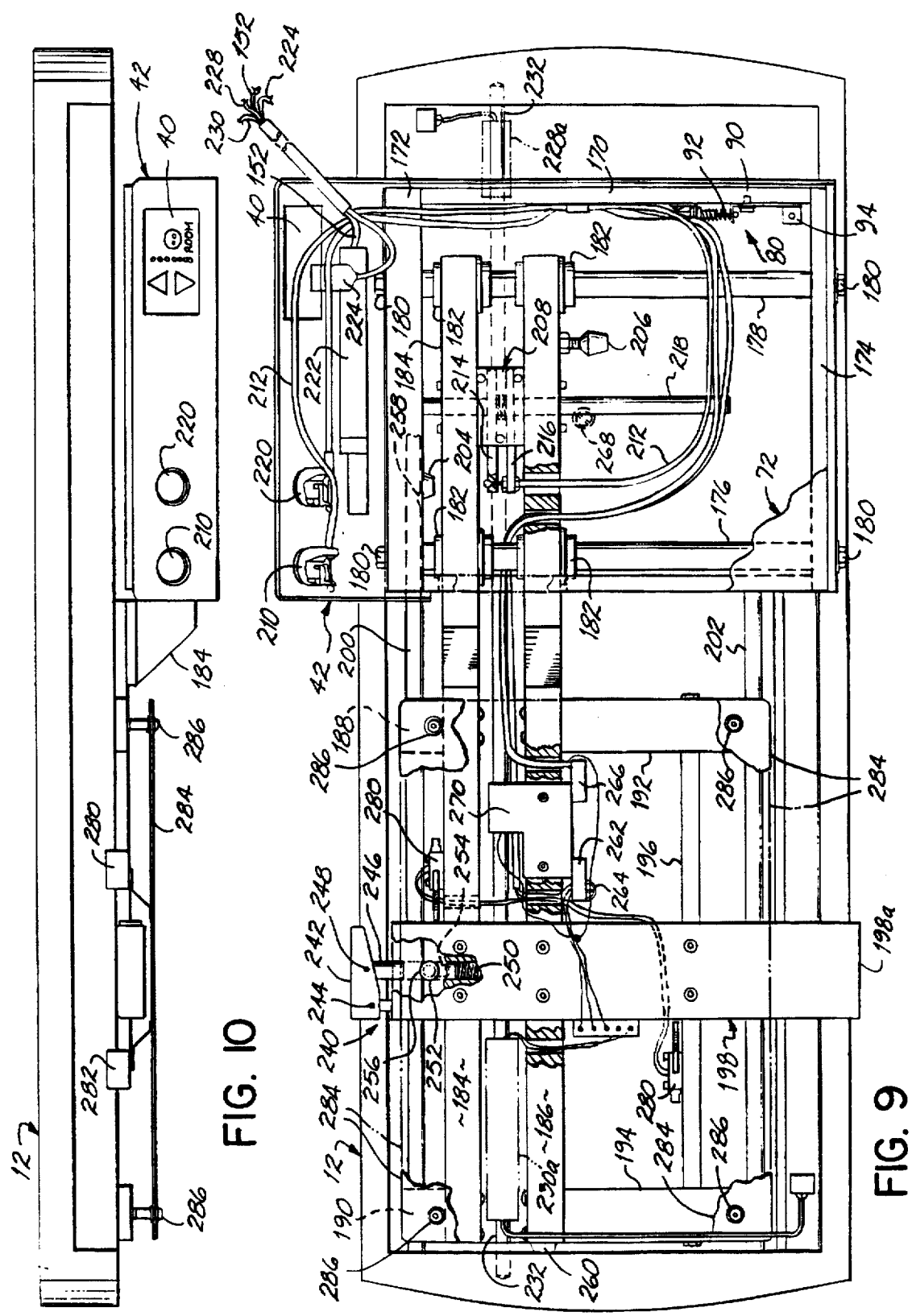

OPHTHALMIC INSTRUMENT SUPPORT AND LIGHTING SYSTEM

BACKGROUND OF THE INVENTION

The present invention generally relates to ophthalmic stands and lighting systems designed to work in conjunction with such ophthalmic stands. The invention is more particularly directed to a unique adjustable instrument delivery table and a programmable room lighting system which operates in conjunction with various ophthalmic instruments.

In the practice of ophthalmology, it has been common for both the doctor and patient to be seated and to provide the doctor with an instrument delivery table which may hold two different ophthalmic instruments. The table may be shifted between two positions to present one or the other of the instruments directly in front of the patient. Various prior systems have been proposed and utilized and some of these systems allow the instrument delivery table to be rotated into position in front of the patient while others allow the table to be moved laterally from a stored position into an operative position in front of the patient. An example of an ophthalmic instrument support which allows three distinct movements including rotational movement from a stored position to an operative position, longitudinal movement to present one or the other of two ophthalmic instruments in front of the patient and vertical movement to allow adjustment of the instruments relative to the height of the patient and the doctor is found in U.S. Pat. No. 4,643,547.

Drawbacks of prior instrument delivery tables include difficulty in adjusting the various positions of the table, including the inability to infinitely adjust within a predetermined range of movement as well as the lack of an ability to adjust the position of the table toward and away from the patient in a direction perpendicular to the longitudinal movement between the two instrument positions. This would be helpful, for example, to accommodate for the various size ranges of patients that will be seated in the examining chair.

Various ophthalmic examination systems have also included lighting control systems which adjust the room lights to a preset intensity when a particular instrument is activated. These systems have generally been designed so that the activation of a given instrument automatically sets the room lighting conditions in accordance with a dimmer which is preset and prewired to the particular instrument. The main drawback of such systems has been the inability of the doctor to easily program each of the many instruments and electrical controls to activate a desired room lighting condition in accordance with his or her particular needs or desires. Also, these systems have generally been hard wired into the room lighting wiring and are therefore more susceptible to various noise related problems in more complex systems. Such previous lighting control systems may be found in U.S. Pat. No. 3,724,931 and U.S. Pat. No. 3,832,041 as well as in the model 905 "Pendulum Delivery System" sold by Reliance Medical Products, Inc. of Mason, Ohio.

It would therefore be desirable to provide an ophthalmic instrument delivery system as well as a programmable lighting system which would make examination of a patient by a doctor easier and which would provide for easier and fuller adjustment of both the instrument table and the room lighting conditions according to any specific doctor's requirements.

SUMMARY OF THE INVENTION

The present invention provides a uniquely position adjustable instrument support table for use in conjunction with an examining chair and a lighting system which allows the user to program the desired room lighting independently for each of several instrument switches, examination lights or other electrical devices used during an ophthalmic examination.

In accordance with a first aspect of the invention, the ophthalmic instrument support table includes a base unit and a table top mounted to the base unit by support structure allowing four degrees of freedom to adjust the location of the table top with respect to both the patient seated in the chair and the doctor examining the patient on the opposite side of the table. Specifically, the table top is mounted to the base unit by support structure including a movable support which allows the table top to be moved from a stored position located in front of the base unit to an operative position located adjacent to the examining chair. The support structure further includes a first adjustable support and locking mechanism for moving the table top along a first horizontal path and locking the table top in a selected position along that first horizontal path. A second adjustable support and locking mechanism is provided for moving the table top along a second horizontal path which is transverse and preferably perpendicular to the first horizontal path and which allows locking of the table top in a selected position along that second horizontal path. A third adjustable support and locking mechanism is provided for moving and locking the table top selectively within a vertical path. The second and third adjustable support and locking mechanisms are infinitely adjustable along their respective paths of movement.

The movable support which allows the table top to be moved from the stored position to the operative position is preferably a pivot connection and, more specifically, includes two rotating arms connected between the table top and the base unit. This movable support actuates at least one switch as it moves from the stored position to the operative position and this switch may be used to cause power to be directed to the instruments located on the table top.

The first adjustable support and locking mechanism allows the table top to be moved in a side-to-side fashion along the lengthwise dimension of the table top to position one or the other of the instruments on the table top in front of the patient. Switches are provided at each of the two positions to activate or provide power to the particular instrument located in front of the patient.

In a second aspect of this invention, a programmable lighting system is provided which allows the doctor to easily program the room lighting conditions such that a programmed room lighting intensity is effected upon activation of any of a plurality of input devices, such as instruments, lights, switches or other electrical devices used by the doctor during the examination. Thus, unlike past systems, the doctor may easily set the room lighting conditions according to his or her particular desires and need not be forced to use factory preset lighting conditions.

Specifically, in a single zone option of the lighting control the doctor may quickly enter a programming mode and then activate a particular input device to inform the control that that particular device is being programmed to effect a certain lighting intensity of the room lights. The doctor uses a room lighting intensity control to adjust the room lighting conditions for that given input device. When the input device is deactivated, the programmed lighting condition for that input device is saved into volatile or nonvolatile memory and each subsequent activation of the input device automatically activates the programmed room lighting intensity. A dual zone option is also provided and allows programming of up to sixteen different "scenes" utilizing two different banks or circuits of room lights. For example, one bank of lights might be incandescent and one may be fluorescent. Each circuit of lights may be adjusted in intensity and saved in the control as a "scene". Each input device may then correspond to and activate a different programmable "scene".

An infrared transmitter is located on the ophthalmic instrument system of the present invention and communicates with an infrared receiver in a conventional lighting control box which may be placed on the wall of the examination room. The infrared transmitter conveniently clips to the instrument pole of the system and may be adjusted vertically on the pole as well as rotationally to allow proper communication with the lighting control box on the wall. The infrared transmitter is generally C-shaped such that it may be received in a sliding fashion on the pole. The transmitter includes a plurality of spaced LEDs which send the infrared signals outwardly in a generally pie shaped pattern to also insure good reception at the receiver. A fixation light box may optionally be attached to the wall opposite the patient and may receive infrared signals from the transmitter as directed by the control and the input from the doctor.

These and other advantages of the present invention will become more readily apparent to those of skill in the art upon review of the following detailed description of the preferred embodiments taken in conjunction with the accompanying drawings.

BRIEF DESCRIPTION OF THE DRAWINGS

FIG. 7 is a side elevational view of the table top and base unit showing the table top in a raised position;

FIG. 8 is a side elevational view of the table top and base unit showing the table top in a lowered position;

FIG. 9 is a bottom view of the table top and its base support structure;

FIG. 10 is a side elevational view of the table top and its base support structure;

DETAILED DESCRIPTION OF THE PREFERRED EMBODIMENTS

Figure 1:
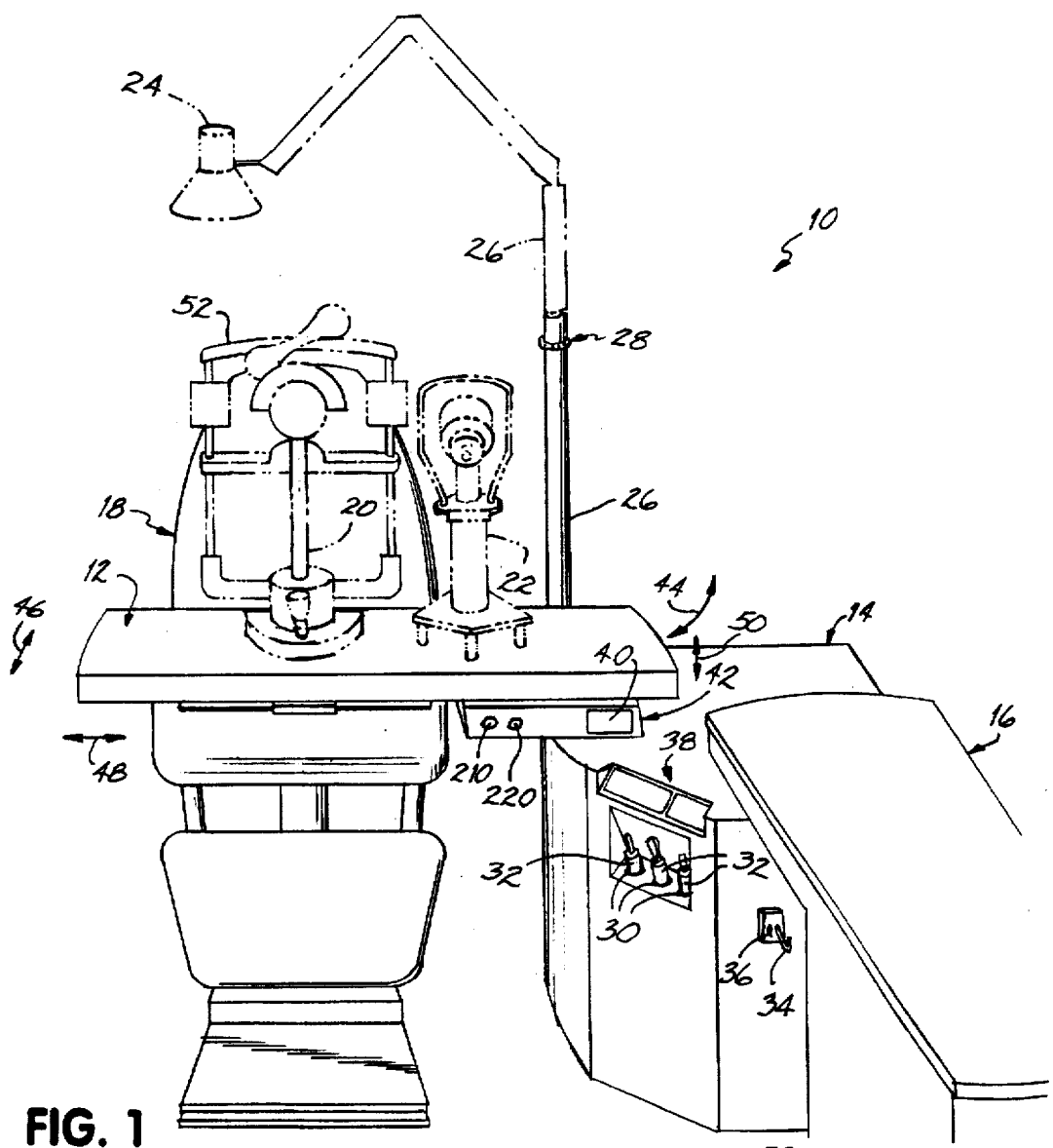
FIG. 1 is a diagrammatic perspective view of the instrument support table of the present invention with the table in operative position in front of an examining chair.

Referring first to FIG. 1, an ophthalmic instrument and programmable lighting system 10 constructed in accordance with a preferred embodiment of the invention is shown. System 10 includes an adjustable table top 12 which is connected to a base unit 14. System 10 may also include a desk 16 which may be used for various purposes by the doctor. Table top 12 is movable from a stored position directly over top of base unit 14 to the operative position shown as directly in front of a patient seated within an examining chair 18. Table top 12 may include, for example, two ophthalmic instruments 20, 22. These instruments may, for example, be a conventional slit lamp 20 and keratometer 22. System 10 further includes an overhead lamp 24 which is mounted to a pole 26. Also mounted to pole 26 is an infrared transmitter 28 for use in sending infrared signals to a lighting control box and a fixation light box as will be described further below in the discussion of the programmable lighting control system. Three instrument wells 30 are provided for holding and recharging three respective instruments 32 for use by the doctor. The wells 30 each contain a conventional sensing circuit that senses when the instrument 32 has been placed into and withdrawn from its respective well 30 as will be discussed below. A hook or binding post 34 is provided on base unit 14 for holding an indirect ophthalmoscope (not shown). A toggle switch 36 is provided next to hook 34 for controlling the room lights as will be described below. Hook 34 is also part of a switch which activates the indirect ophthalmoscope upon removal of the instrument from hook 34.

A main control panel 38 is mounted to base unit 14 for controlling the fixation lights, the indirect ophthalmoscope, overhead lamp 24, the room lights, chair 18, etc., as will be described further below. A smaller control panel 40 is disposed on table base 42 and, for example, includes switches for controlling the room lights as well as the intensity of the slit lamp bulb switches (not shown) may also be provided to control chair 18.

As will be described in detail, table top 12 is capable of being rotated from a stored position directly over top base unit 14 to the operative position shown generally along a path indicated by arrow 44. In addition, table top 12 is capable of being infinitely adjusted along a predetermined range of movement toward and away from examining chair 18 generally along the path indicated by arrow 46. Table top 12 is further capable of being shifted side-to-side as indicated by arrow 48 between two positions. One position places instrument 20 in front of the patient seated in chair 18 having his or her chin resting on chin rest 52 and the other of these positions places instrument 22 in front of the patient with chin rest 52 remaining stationary as table top 12 is moved. Finally, table top 12 is also capable of being infinitely adjusted in a vertical path indicated by arrow 50 and along a predetermined range of movement.

Figure 2:
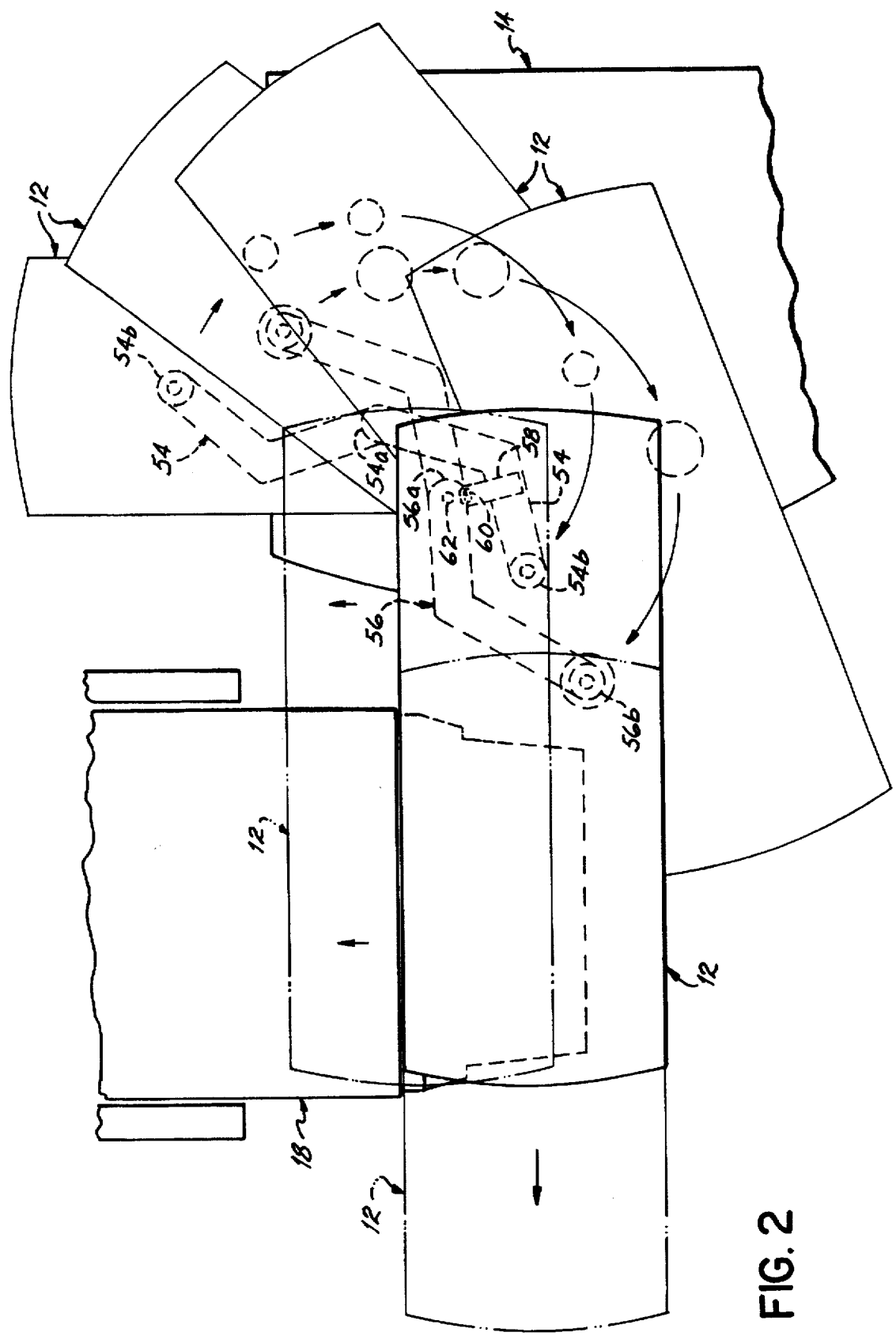
FIG. 2 is a diagrammatic top view of the examining chair and the instrument support table being moved between the stored position and the operative position.

FIG. 2 schematically illustrates the movement of table top 12 between a stored position in which table top 12 is disposed directly above base unit 14 and along one side of chair 18. A pair of pivoting arms 54, 56 carry table top 12 from the stored position to the operative position as shown with table top 12 finally disposed directly in front of chair 18. One arm 54 carries a locking plate 58 having a slot 60 which engages a spring loaded pin 62 carried by the other arm 56 to lock table top 12 into the operative position.

Figure 3:
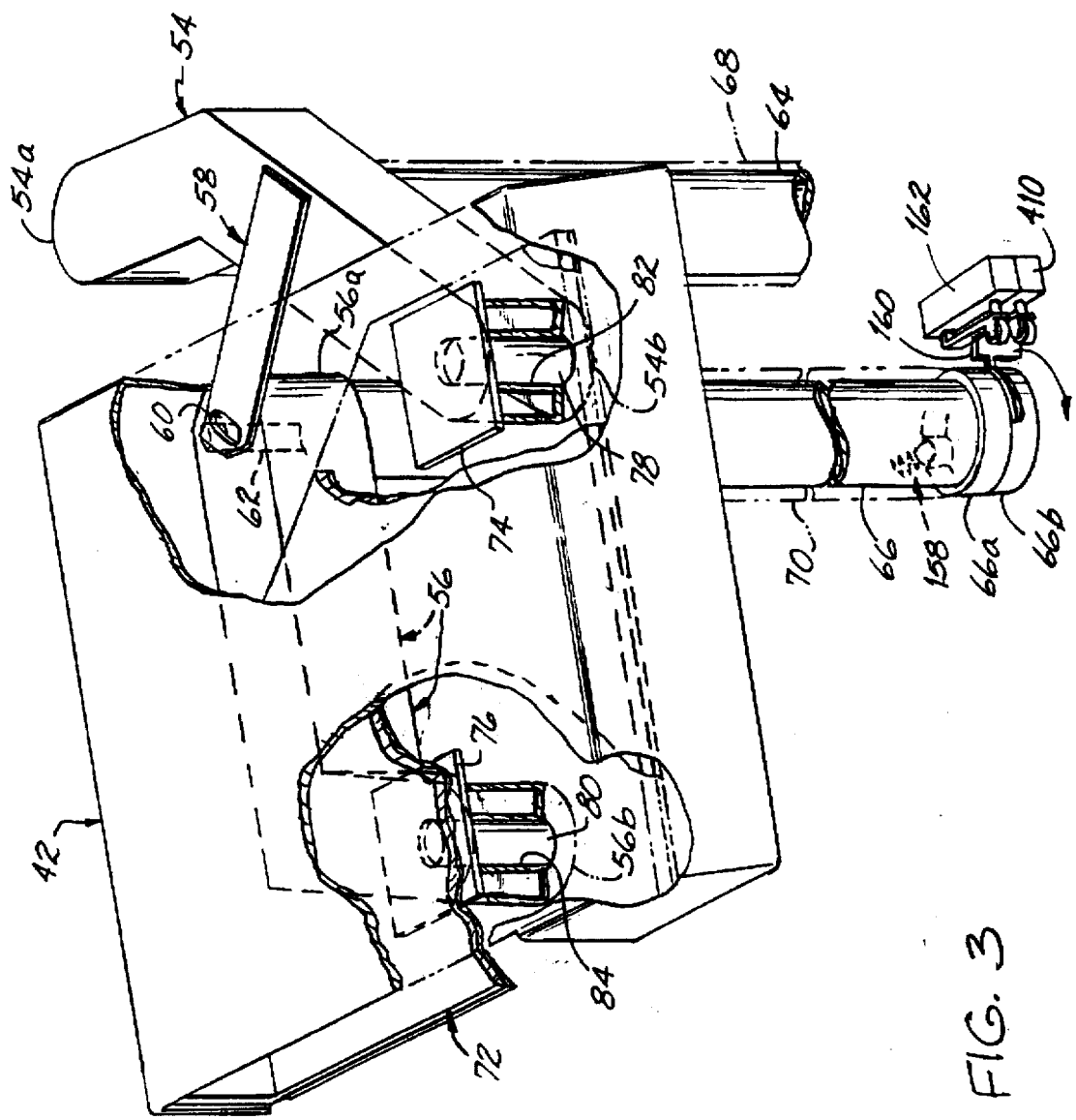
FIG. 3 is a partially fragmented perspective view of the table base support structure and the pivoting arms which allow movement of the table between the stored and operative positions.

Referring now to FIG. 3, the connections between table base 42 and arms 54, 56 are shown. Arms 54, 56 include inner pivoting ends 54a, 56a which are rigidly secured to the tops of respective vertical rods 64, 66. Rods 64, 66 are contained for rotation within cylindrical tubes 68, 70. Outer ends 54b, 56b of arms 54, 56 are secured to the underside of a plate 72 which forms part of table base 42. Specifically, plates 74, 76 are rigidly attached to the underside of plate 72, as by welding, and plates 74, 76 include respective pins 78, 80 secured thereto in a rigid manner such that pins 78, 80 extend vertically downward. Pins 78, 80 are received within cylindrical holes 82, 84 in ends 54b, 56b of arms 54, 56. Thus, as table base 42 and table top 12 (FIG. 1) are rotated and arms 54, 56 pivot with rods 64, 66 rotating within tubes 68, 70, relative rotation takes place between pins 78, 80 and ends 54b, 56b.

Figure 4:
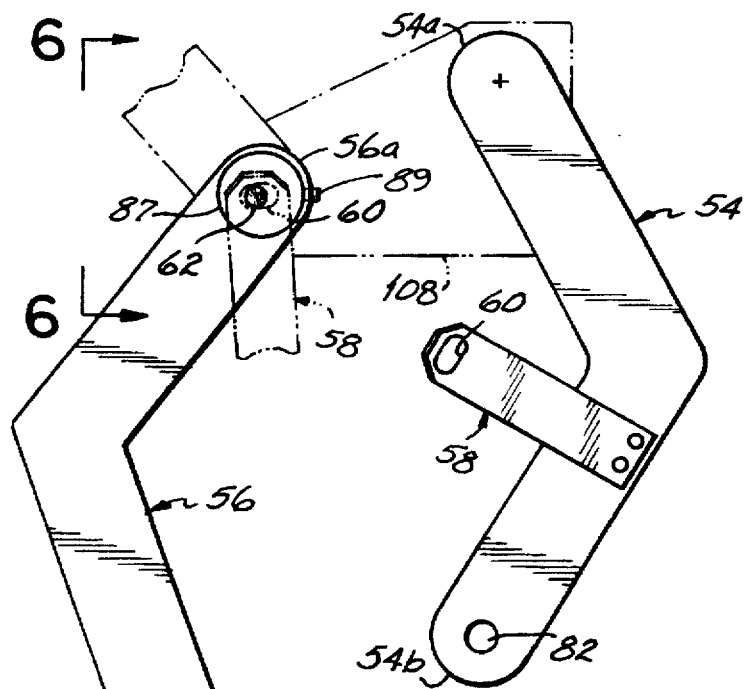
FIG. 4 is a schematic top view of the pivoting arms and the locking mechanism used for locking the table top in the operative position.
Figure 5:
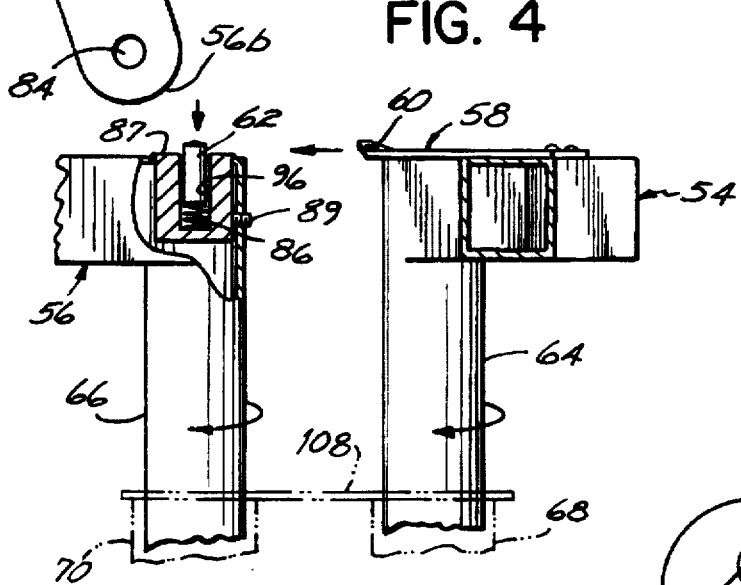
FIG. 5 is a schematic side elevational view of the pivoting arms and also illustrating the locking mechanism shown in FIG. 4.
Figure 6:
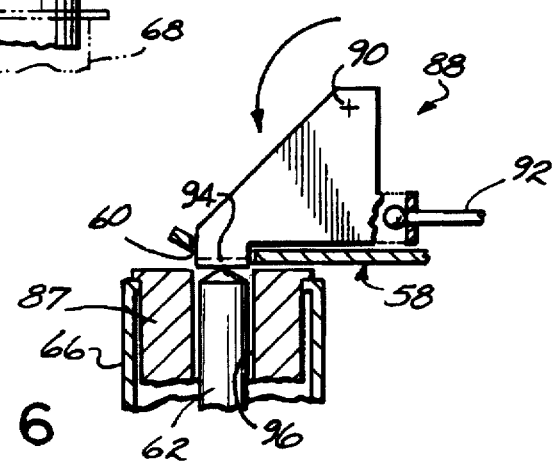
FIG. 6 is an enlarged detail showing the release mechanism which may be actuated to unlock the table top from the operative position.

Referring now to FIG. 3 taken in conjunction with FIGS. 4–6, arms 54, 56 are locked together by a locking plate 58 when table 12 reaches the operative position (FIG. 1). As shown best in FIG. 5, locking plate 58 rides up over spring loaded pin 62 and compresses spring 86 until pin 62 registers within slot 60 of plate 58. The pin 62 and compression spring 86 are more specifically in an eccentric 87 which is mounted within end 56a of arm 56. The eccentric allows the pin to be adjusted to account for misalignment with locking plate 58, so that the arms 54 and 56 are at the extreme end of their in use travel to allows for more stable securement in the operative position. When the alignment of the eccentric is achieved, a set screw 89 is tightened to secure eccentric 87 in position. As shown in FIG. 6, a release mechanism 88 is provided within table top 12 (FIGS. 1 and 10) and is used to depress spring loaded pin 62 to release its locking engagement with plate 58. Specifically, release mechanism 88 includes a pivot connection 90 about which release mechanism 88 rotates when a cable 92 is pulled. This causes end 94 of release mechanism 88 to depress spring loaded pin 62 into its receiving bore 96 thereby releasing its engagement within slot 60 of plate 58. This allows movement of table top 12 back into the stored position generally along the path illustrated in FIG. 2. The actuation and specific location of attachment of the release mechanism 88 will be described further below with reference to FIG. 10.

The vertical adjustment of table top 12 will now be described with respect to FIGS. 7 and 8. FIG. 7 shows table top 12 in a fully raised position while FIG. 8 shows table top 12 in a fully lowered position. Infinitely adjustable movement is allowed between these two positions. The mechanism for allowing this vertical adjustment is contained within base unit 14. Much of the supporting structure of base unit 14 has been deleted for clarity in FIGS. 7 and 8 but generally comprises frame members, such as frame members 98, 100, 102 as well as upper and lower panels with only lower panel 104 being shown in the drawings. Casters 106 may also be provided for easier movement of base unit 14.

It will be appreciated from a review of FIGS. 7 and 8 that the tubes 68, 70 which receive rods 64, 66 for rotation are raised and lowered with respect to base unit 14. To this end, tubes 68, 70 are rigidly secured together at their respective upper ends by a connecting plate 108 and are rigidly secured together at their lower ends by horizontal plates 110, 112 as well as vertical plates, with only one vertical plate 114 being shown. Vertical plates 114 are secured to upper and lower bushings 116, 118 which receive vertical rods 120, only one of two rods 120 being shown in the drawings. A counterweight system 122 is provided to assist the operator in raising table top 12 and the various components connected thereto. Counterweight system 122 comprises two counterweights 124, 126 attached to cables 128, 130 and received for vertical movement along respective vertical rods 132, 134. Cables 128, 130 extend upwardly over respective pulleys 136, 138 and over a double pulley 140. The ends of cables 128, 130 opposite to counterweights 124, 126 are attached to a cable mount 142 which is rigidly secured to plate 110.

Another vertical rod 144 is provided within base unit 14 and receives a conventional locking mechanism 146. Locking mechanism 146 comprises a pair of plates 148, 150 which receive rod 144 through aligned bores in each plate 148, 150. The ends of each plate 148, 150 are connected to a cable 152 while the opposite ends are received between a pair of pins 154. Another pin 156 is disposed on the opposite side of vertical rod 144 and between plates 148, 150. A spring 153 is received about vertical rod 144 and between plates 148, 150 to provide a normal spring bias of plates 148, 150 into a unparallel orientation thus effectively jamming plates 148, 150 against vertical rod 144 and preventing any vertical movement of table top 12. When cable 152 is pulled via a push button associated with table top 12 to be described below, plates 148, 150 are moved into a parallel orientation against pins 154, 156 with respect to each other as shown in FIGS. 7 and 8 thus vertically aligning the holes in plates 148, 150 and allowing vertical movement of locking mechanism 146 along vertical rod 144.

As further shown in FIGS. 3, 7 and 8, a pair of cams 66a, 66b are secured to the bottom of rotatable rod 66. One of these cams 66a acts as a detent mechanism to positively restrain table top 12 in the stored position with a ball and spring assembly 158 while the other of these cams 66b actuates a switch 162 by way of a small lever switch 162 instructs the control, to be described below, to provide power to the instruments located on table top 12 (FIG. 1).

The support structure which allows both the side-to-side shifting of table top 12 in front of chair 18 as well as the adjustment of table top 12 both toward and away from examination chair 18 (FIG. 2) will now be described with reference to FIG. 9. Table base 42 generally comprises a supporting frame 170 which includes front and rear support rails 172, 174. A pair of guide rods 176, 178 are rigidly fastened between front and rear support rails 172, 174 by respective bolts 180. Guide rods 176, 178 each carry two sliding bearings 182. One bearing 182 on each guide rail 176, 178 is rigidly secured to one of a pair of support arms 184, 186 which extend lengthwise beneath table top 12. Support arm 184 is further connected to a pair of short bearing support members 188, 190 and support arm 186 is rigidly secured to a pair of long bearing support members 192, 194. A cross member 196 is also bolted between the pair of long bearing support members 192, 194. A chin rest support plate 198 is bolted to the underside of arms 184, 186 and cross member 196. One end 198a serves a mounting location for chin rest 52 (FIG. 1). Bearings (not shown) contained respectively within short bearing support members 188, 190 and long bearing support members 192, 194 receive guide rods 200, 202 in a sliding manner. Guide rods 200, 202 are suitably secured to the movable table top 12 in a rigid manner. Thus, in a manner to be described more completely below, it will be appreciated that table top 12 and its attached guide rods 200, 202 may shift from right to left as viewed in FIG. 9 with respect to bearing support members 188, 190, 192, 194, arms 184, 186 and table base 42.

Front and rear adjustability of table top 12 is provided by the sliding movement of arms 184, 186 along guide rods 176, 178 and within the limits established by bumpers 204, 206. This will simultaneously adjust the position of table top 12, rods 200, 202, members 188, 190, 192, 194, 196, 198 and chin rest 52 (FIG. 1) with respect to the remaining structure of base 42. Bumper 204 will be contacted by arm 184 at one end of the range of movement while bumper 206 will contact rear support rail 174 at the other end of the range of movement. A locking mechanism 208 identical to locking mechanism 146 described with respect to FIG. 8 is provided for locking table top 12 into a desired position within this range of movement. Locking mechanism 208 is operated by a push button 210 extending through an outer surface of table base 42. Specifically, push button 210 pulls a cable 212 which pivots two plates 214, 216 into a parallel relationship with respect to each other thereby allowing sliding movement along rod 218 as previously described. As also previously described, when push button 210 and cable 212 are released, plates 214, 216 return to their normally biased unparallel orientation by a spring 217 thereby jamming against rod 218 and preventing movement of bearings 182 along guide rods 176, 178.

A second push button 220 is provided on table base 42 for operating the previously described release mechanism 88 (see FIG. 6). Specifically, when push button 220 is depressed, cable 92 pulls against and pivots release mechanism 88 about pivot connection 90 with table base 42 and moves end 94 into engagement with pin 62 (FIG. 6). This releases table top 12 from the operative position and allows the doctor to move it back into the storage position (FIG. 2).

A pivotal lever 222 is also provided beneath table base 42 and pulls cable 152 when squeezed upwardly by the user. As previously described with respect to FIGS. 7 and 8, cable 152 operates the locking mechanism associated with the vertical adjustment of table top 12. Therefore, cable 152 is shown extending away from table 12 with the understanding that it is appropriately directed into base unit 14 as shown in FIGS. 7 and 8.

Also leading into table base 42 from, for example, base unit 14 is a cable assembly 224 connected with the control system to be described and leading to control panel 40 on table base 42 (FIG. 10). In addition, both high and low voltage cable assemblies 228, 230 extend into table base 42 for respectively powering instruments 20, 22 (FIG. 1) in the instance where one of these instruments requires high voltage power and one requires low voltage power. High and low voltage cable assemblies 228, 230 include coil portions 228a, 230a which are received about a guide rod 232 and which respectively extend and contract with the left and right shifting movement of table top 12 as viewed in FIG. 9.

The shifting of table top 12 right to left as viewed in FIG. 9 is controlled by a release mechanism 240 which generally comprises a handle 242 attached by a pivot connection 244 with chin rest support plate 198. A pin 246 is also connected to handle 242 by a pivot connection 248 at one end and bears against a compression spring 250 at the opposite end. Pin 246 carries a roller 252 extending outwardly therefrom and outwardly of a slot 254 within plate 198. Roller 252 registers within a detent 256 in guide rod 200 to lock table top 12 into the position shown in FIG. 1 with instrument 20 aligned with a patient sitting in chair 18. Another detent 258 is located in guide rod 200 and defines the second position of table top 12 in which instrument 22 is aligned with chair 18. To release table top 12 from one position, handle 242 is depressed to move pin 246 inwardly against spring 250 and move roller 252 out of detent 256. This allows table top 12 to be shifted to the left as viewed in FIG. 9 with roller 252 rolling against guide rod 200 until detent 258 is reached. When detent 258 is reached, roller 252 will snap into place by the force of spring 250. Bumpers may be provided as well to stop the movement of table top 12 at each of these two positions. Only one of these bumpers 260 has been shown in FIG. 9.

In the first position shown in FIG. 9, a switch 262 is activated by a fastener head 264 located on the underside of table top 12. When switch 262 is activated in this manner, power is supplied by the low voltage cable assembly 228 to instrument 20 and power is not supplied instrument 22 (FIG. 1). When table top 12 is shifted to the second position such that roller 252 registers within detent 258, a second switch 266 is activated by a second fastener 268 located on the underside of table top 12. This deactivates switch 262 thereby cutting off power to instrument 20 and activates switch 266 thereby supplying power from the other of the high and low voltage cable assemblies 228, 230 to instrument 22 (FIG. 1). In the preferred embodiment shown, this position will supply power from cable assembly 230. Switches are mounted to a plate 270 and may, for example, be obtained from Cherry Electrical Products located in Waukegan, Ill. and sold under part number E31-00K.

Finally, table top 12 is also provided with a mechanism for preventing inadvertent raising of chair 18 into table top 12. In this regard, and referring now to both FIGS. 9 and 10, a pair of switches 280, 282 are respectively mounted to arm 184 and cross member 196 and are designed to be activated by a plate 284 connected to the underside of table top 12 by spring loaded fastener assemblies 286. As will be appreciated by a review of FIG. 10, if chair 18 (FIG. 1) is raised to such an extent that the patient's lap contacts and pushes against plate 284, one or both of switches 280, 282 will be activated and will send a signal to the control system, to be described below, which will then either stop all movement of the chair or reverse the movement of chair 18. Switches 280, 282 may also be obtained from Cherry Electrical Products under part number E31-50K.

Figure 11:
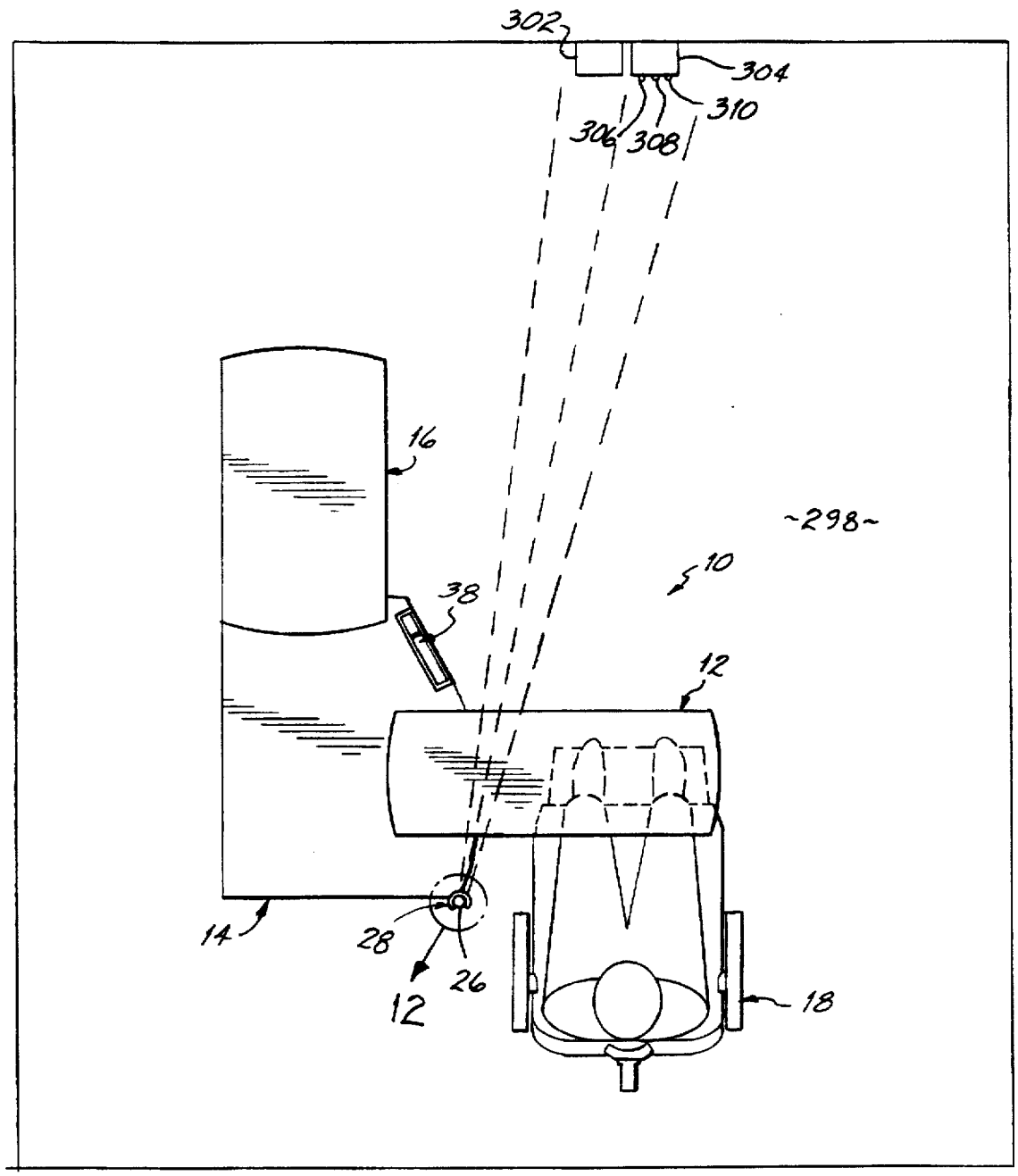
FIG. 11 is a diagrammatic top view of an examination room showing the relative positions of the instrument support table, the patient, and the various lighting control components of the present invention.

Referring now to FIG. 11, a schematic layout of an examination room 298 is shown incorporating the instrument delivery system and programmable lighting system 10 of the present invention. As will be described below, base unit 14 preferably contains the various electrical hardware and control components of the programmable lighting system except for the infrared transmitter 28 which is mounted to instrument pole 26 and which communicates with receivers contained within a room lighting control box 302 and a fixation light control box 304 mounted on one wall of room 298. Fixation light box 304 includes three fixation lights 306, 308, 310 which some doctors use for certain examination procedures in which the patient seated in chair 18 is told to focus on one of the lights 306, 308, 310. Fixation lights 306, 308, 310 may optionally be those stand alone units with separate receivers that the doctor could place anywhere in room 298.

Figure 12:
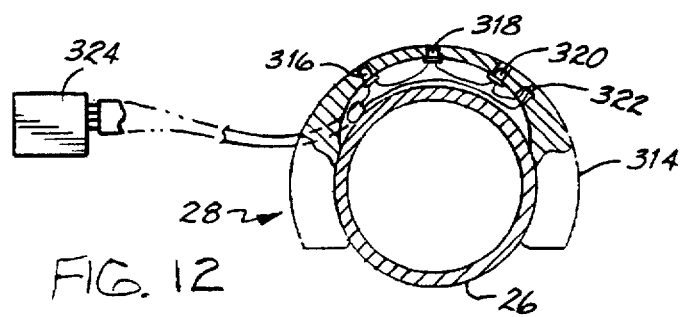
FIG. 12 is an enlarged detail of the infrared transmitter of the lighting control system of the invention.

As shown in more detail in FIG. 12, the unique infrared transmitter 28 of the present invention includes a generally C-shaped body 314 which simply clips onto pole 26 (FIGS. 1 and 11). Body 314 is sized to allow sliding movement along pole 26. Three angularly spaced LEDs 318, 320, 322 are incorporated into the C-shaped body 314 for transmitting the infrared signals to respective receivers contained in boxes 302, 304. A fourth LED, which may be red in color, may also be included to indicate activation of transmitter 300. A suitable, conventional wire and plug assembly 324 extends from body 314 and is connected to a central processing unit of the control to be described.

Figure 13:
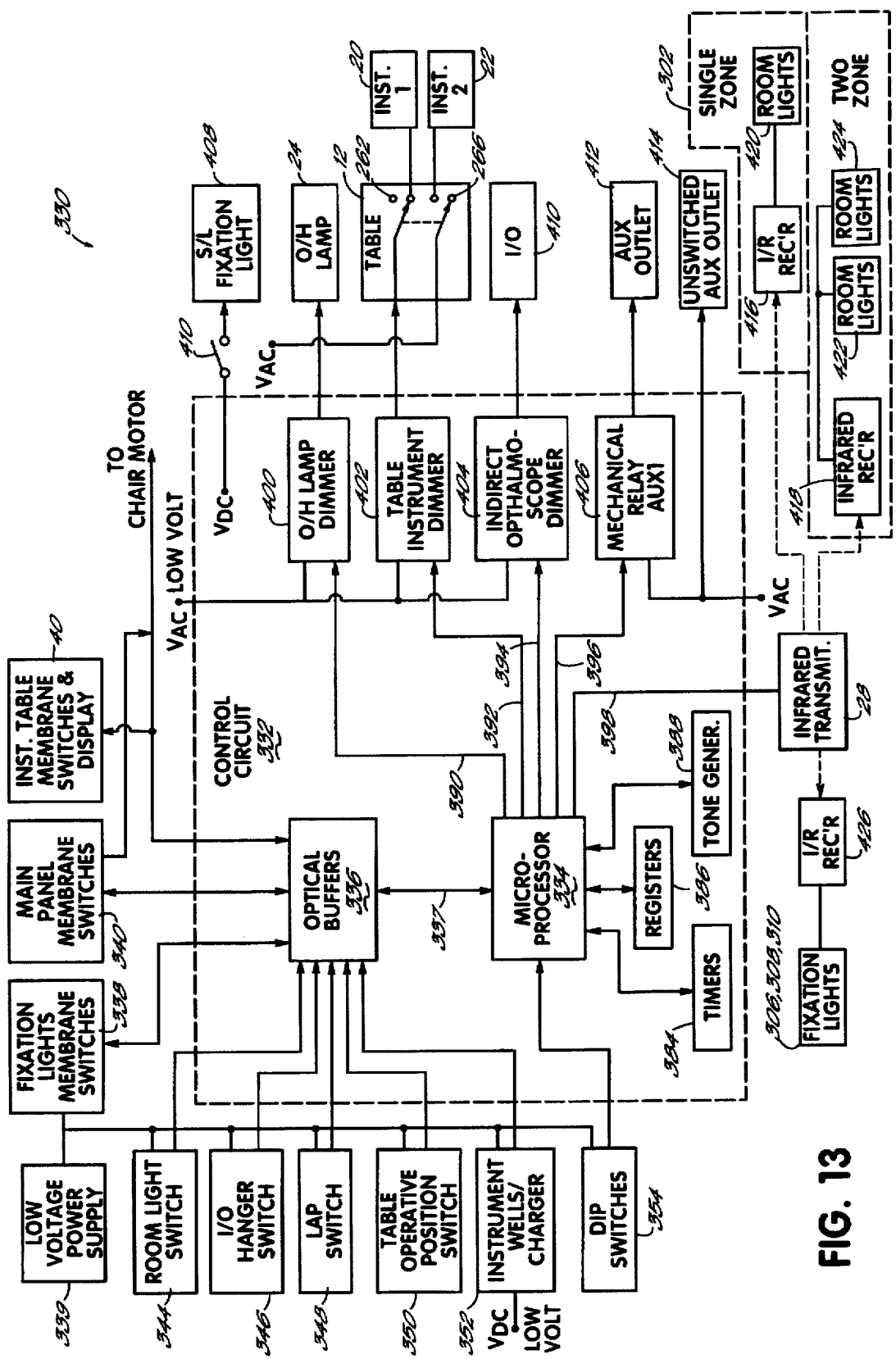
FIG. 13 is a schematic block diagram of a control system for operating the various electrical components, including the lighting control components of the invention.

With reference now to FIG. 13, a block diagram of a control system 330 constructed in accordance with the present invention is shown. Control system 330 includes a control circuit 332 based around an 8 bit microprocessor 334 (Microchip Technology, Chandler, Ariz. under part number P1C16C64) which controls overall operation of the control system 330. Preferably, microprocessor 334 and related control logic are mounted on a conventional printed circuit board and comprise control circuit 332. This conventional hardware, including the other necessary, conventional and electrical control components such as a power entry module, fuses, and a transformer may be mounted in base unit 14. As will be described in more detail below with reference to FIG. 15, microprocessor 334 is responsive through conventional programming techniques to various switch inputs. Representative switch inputs include those received from fixation light membrane switches 338, main panel membrane switches 340 and instrument table membrane switches 40 (also see FIG. 10). Main panel switch plates 338, 340 form main control panel 38 as shown in FIG. 1 and are described further below with respect to FIG. 14.

Further switch inputs include a room light switch 344 which enables ophthalmoscope hanger switch 346 associated with hook 34 in FIG. 1 to control the room lights in an operator programmable manner. When switch 344 is in one position, activation of switch 346 will cause a programmed room lighting condition to occur and when switch 344 is in the other position, room lighting conditions will not change. A lap switch 348 (representing switches 282, 284 in FIGS. 9 and 10), a table operative position switch 350 (representing switch 162 in FIGS. 7 and 8), instrument well sensor circuits 352 associated with each of the instrument wells 30 (FIG. 1), and dip switches 354 are representative of but not necessarily all inclusive of additional input devices into microprocessor 334. As shown in FIG. 13, all switch inputs except for dip switches 354 are operatively connected to microprocessor 334 through optical buffers 336 (Sharp PC847). The optical buffers 336 provide an interface circuit which electrically isolates the various switch inputs connected thereto from the microprocessor terminals connected to input and output lines 337. In this way, only a low voltage signal from a power supply 339 in a preferred range of +5 V—+12 V is used to operate the system from the various switch inputs.

Figure 14:
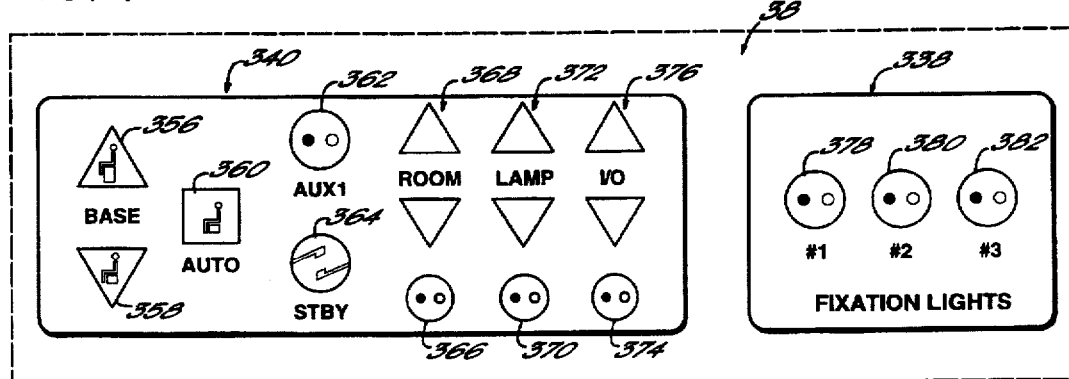
FIG. 14 is a top view of the main control panel used for operating the various electrical components of the system, including the programmable lighting control system.

Dip switches 354 may be used to configure control circuit 332 to the preferences of the user and, for example, the various power requirements of different electrical components. With respect to the present invention, dip switches may be used to enable and disable room lighting programmability associated with the various switches, instruments, etc. Dip switches 354 may also be used to indicate to the control that switch 346 has been installed and this will override switch 376 on control panel 38 (FIG. 14). Dip switches 354 may further be used to control voltage sent to certain instruments in cases, for example, in which a type of instrument may use a bulb requiring 6 volts or 7 volts.

Referring now briefly to FIG. 14, switch plate 340 of main control panel 38 includes three switches for operating the examination chair 18 (FIG. 1) in a conventional manner. These switches include a chair raising switch 356, a chair lowering switch 358 and an "auto" switch 360 which lowers chair 18 to a lower limit of the chair travel to allow the Patient to exit. Switch plate 340 further includes an "AUX1" switch 362 which turns either 115 V or 230 V on and off to an "AUX1" outlet 412 in FIG. 13 associated with the system 10. In practice, the primary purpose of this switch is to turn a projector on and off, however, it might be used for any instrument which runs on 115 V or 230 V power. A standby switch 364 is also provided on main switch plate 340. The standby switch turns secondary power on and off to system 10. Specifically, this switch may be designed to cause 115 V or 230 V to be applied to an "AUX2" outlet as well as a keratometer outlet.

Main switch plate 340 further includes on/off switches 366, 270, 274 for respectively turning the room lights, overhead lamp 24 (FIG. 1), and an indirect ophthalmoscope (not shown) associated with binding post 34 (FIG. 1) on and off. In addition, each of these switches 366, 370, 374 include corresponding intensity adjustment switches 368, 372, 376 for respectively varying the intensity of the room lighting, overhead lamp 24, and the indirect ophthalmoscope bulb. Secondary switch plate 338 of main control panel 38 includes three on/off switches 378, 380, 382 for respectively operating the three fixation lights 306, 308, 310 shown in FIG. 11.

Microprocessor 334 decodes and validates the various switch inputs just described as those of skill in the art will contemplate and is further operatively connected with the necessary timers 384, registers 386 and a tone generator 388. Output signals on lines 390, 392, 394, 396 and 398 are provided on output ports of microprocessor 334 and respectively connect to an overhead lamp dimmer 400, a table instrument dimmer 402, an indirect ophthalmoscope dimmer 404, a mechanical relay 406 and infrared transmitter 28. Dimmers 400, 402, 406 may be conventional and obtained from Sharp Corporation under part number S 102S01. Likewise, mechanical relay may be obtained from Potter Bruinfield under part number RKA. Dimmers 400, 402, 404 are connected to a low voltage AC power supply which preferably supplies power in the range of 0–12 V. Mechanical relay 406 is connected to a high voltage power supply as shown and previously mentioned which may supply either 115 V or 230 V power. An appropriate power supply, such as a DC power supply, may be provided in control circuit 332 and connected to a slit lamp fixation light 408 which is operated by a switch 410 (FIG. 3) when table 12 is moved into the operative position.

As further shown in FIG. 13, dimmers 400, 402, 404 are respectively connected to the overhead lamp 24, table 12 and indirect ophthalmoscope 410. Indirect ophthalmoscope, as mentioned above, may be operated through a switch activated by binding post or hook 34 (FIG. 1). Switches 262, 266 discussed above with reference to FIG. 9 are represented in FIG. 13 as respectively controlling the first and second instruments 20, 22 (FIG. 1). Table instrument dimmer 402 thus provides the same lighting intensity adjustment for each of the light bulbs associated with instruments 20 and 22. High voltage "$V_{AC}$" is connected to the second instrument 22. Mechanical relay 406 provides high voltage power to an auxiliary outlet 412 in a switched manner as previously mentioned. High voltage power to another unswitched auxiliary outlet 414 is also supplied when the system is powered on. AC power is also supplied to overhead lamp 24, table 12, as previously described, and indirect ophthalmoscope 410 as shown in FIG. 13.

The programmable room lighting system of the present invention is based around a conventional room lighting control 302 which may be obtained from Lutron of Coopersburg, Pa. under part number GRX-3002. Room lighting control 302 has the capability to control either a single zone or a dual zone or circuit of lights (two circuits) of lights depending on the needs or desires of the users.

The present invention is capable of utilizing either of these two options as shown in FIG. 13. In accordance with the invention, room lighting conditions are programmable such that the doctor may easily program the desired room lighting condition to occur upon activation of each of several instruments or switches. For example, upon activation of any of switches 344, 346, 350, 352, 362, 364, 378, 380 and 382, the separately programmed room lighting conditions or intensity will automatically change to the programmed state for that particular switch. This programming is discussed further below but essentially, the microprocessor 334 sends a data coded signal to either the infrared receiver 416 associated with the single zone option or the infrared receiver 418 associated with the two zone option of lighting control 302 to instruct the lighting control, which includes the necessary room light dimmers, to adjust the intensity of the single circuit 420 of room lights in the single zone system or the two circuits 422, 424 of room lights associated with the two zone option to the preprogrammed state corresponding to that data coded signal. In the single zone option, the infrared signal simply transmits a data code between zero and 100 with 100 being the most intense lighting condition and zero representing the room lights being off. Such a code is programmed into memory for each of the above mentioned programmable switches in a very easy manner by the doctor as will be described below.

The two zone option of the lighting control 302 includes 16 separate "scenes". With each scene, each circuit of lights is separately adjusted to a desired intensity and the scene is saved into memory in the lighting control 302. With this two zone option, therefore, each scene may represent a desired lighting condition for a given switch or instrument and activation of that switch or instrument will cause microprocessor 334 to send a signal 398 through infrared transmitter 28 which is coded and recognized by lighting control 302 as representing a particular scene out of the sixteen possible scenes. The scenes are programmed at the lighting control 302 in the two zone option in a known manner associated with that commercially available control box. The microprocessor 334 sends the specific data coded signal associated with a particular scene upon activation of a switch or instrument. For example, "scene 1" may correspond to I/O hanger switch 346, "scene 2" may correspond to table operative position switch 350, etc. The doctor may simply be given a list of sixteen possible switches and/or instruments which correspond to the sixteen different scenes in the two zone option and may independently program the scenes corresponding to each instrument or switch.

Microprocessor 334, when instructed by fixation light membrane switches 378, 380, 382 (FIG. 14), sends another appropriate data code through infrared transmitter 28 to infrared receiver 426 of fixation light box 304 (FIG. 11) to cause a particular fixation light 306, 308, 310 to activate. Upon activation of any of switches 378, 380, 382 microprocessor 334 may also send a programmed data code through infrared transmitter 28 to lighting control 302 to adjust the lighting conditions according to the programmed conditions set by the doctor with respect to one or all of the fixation light switches 378, 380, 382. The system may be easily configured such that if a particular switch or instrument has not been enabled to be programmed by the doctor to cause lighting control 302 to adjust the room lights 420 (signal zone) or 422, 424 (dual zone), the room lighting conditions will remain unaffected by activation of the switch or instruments to a fallback condition such as "full on". Also, a default setting is preferably provided at the factory to account for the situation in which a switch which is enabled to be programmed is not actually programmed by the doctor.

Figure 15:
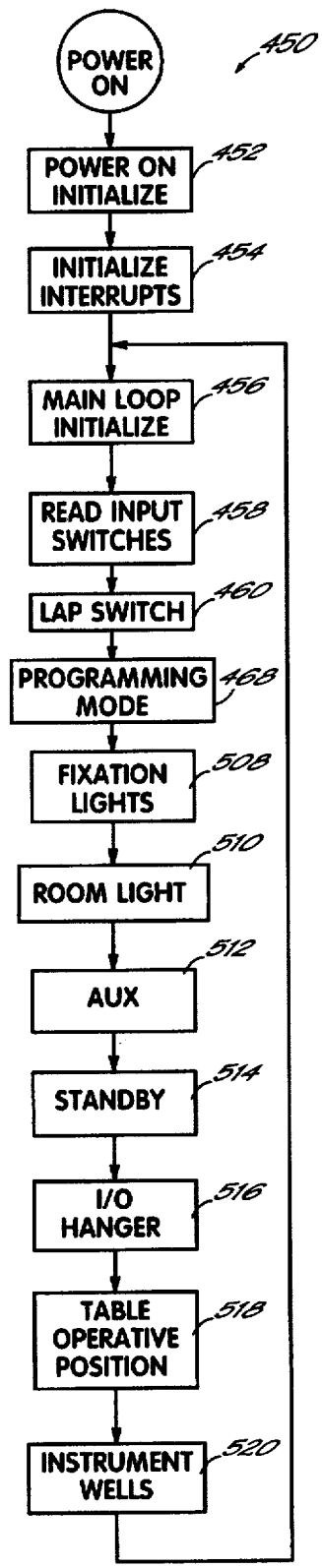
FIG. 15 is a flow chart showing the main routine executed by the microprocessor of the control system shown in FIG. 14.

FIG. 15 is a flowchart illustrating a main routine 450 including process steps executed by microprocessor 334 of control circuit 332. Microprocessor 334 executes the main routine upon application of power to the control circuit 332. The main routine 450 is iterately executed at a suitable rate for the particular application. For example, a main routine cycle loop time suitable for debouncing switches as used in the system 330 is 50 milliseconds. The main routine 450 continuously iterates until the power to control circuit 332 is turned off. At process step 452, main routine 450 initializes the hardware elements of the system such as the timers 384, registers 386, tone generator 388, etc.

Figure 20:
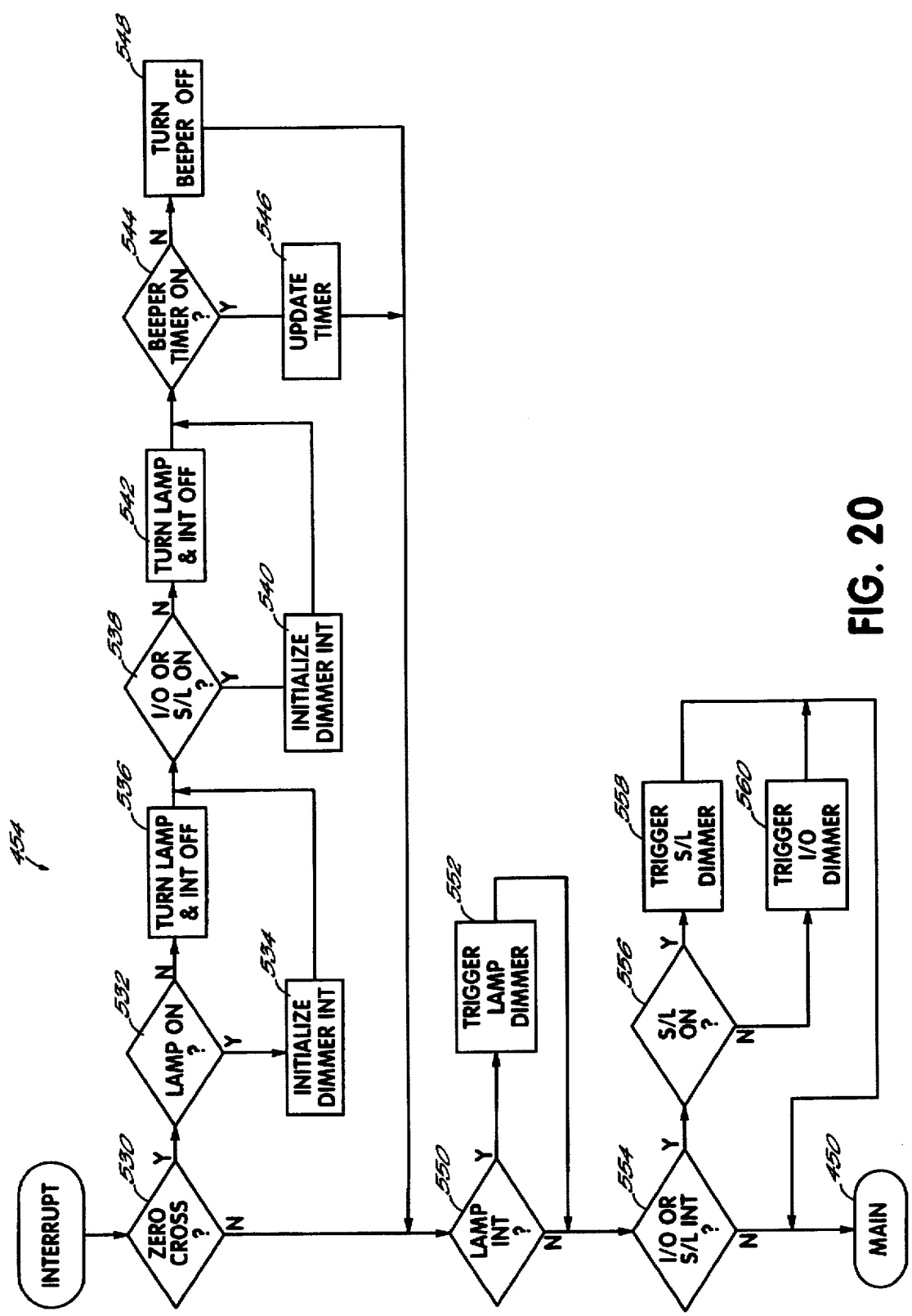
FIG. 20 is a flowchart illustrating an interrupt subroutine of the main routine illustrated in FIG. 15.

FIG. 20 illustrates a flowchart of a subroutine 454 which is the next step in main routine 450 and is used for initializing various interrupts associated with control circuit 332. Specifically, at process step 530, a "zero cross" check is performed approximately every 8 milliseconds and checks to establish whether an AC voltage associated with microprocessor 334 has "crossed through zero", i.e., whether the sine wave of the 50 or 60 Hz line frequency has crossed through the zero point. This is a conventional, reliable method of timing in control circuits such as control circuit 332. If the zero point has been crossed, the process at step 532 detects whether overhead lamp 24 (FIG. 1) is on. If the lamp is on, the process at step 534 initializes a dimmer interrupt associated with dimmer 400 (FIG. 13). The initialization of this dimmer interrupt essentially sets up a timing mechanism to wait a predetermined amount of time, such as 4 milliseconds, to turn dimmer 400 on when control circuit 332 is so instructed. If lamp 24 is not on, the process at step 536 turns the lamp 24 as well as the interrupt off. Next, at process step 538 the process detects whether the indirect ophthalmoscope or the slit lamp are activated. If either the indirect ophthalmoscope or the slit lamp are on, the process at step 540 initializes another dimmer interrupt associated with dimmer 404 (FIG. 13). If the indirect ophthalmoscope and the slit lamp are detected to be off at process step 538, the process at step 542 turns the indirect ophthalmoscope and slit lamp off as well as the interrupt off. Next, at process step 544 the control detects whether a beeper timer is on and, if so, updates the timer at process step 546. If the beeper timer is not detected as being active or on, the beeper is turned off at process step 548. Process steps 536, 542 and 548 are essentially failsafe measures which ensure that the respective components are, in fact, off. If no zero cross is detected at step 53, the process at step 550 determines whether the lamp interrupt has timed out. If the lamp interrupt has timed out, the process at step 552 triggers the lamp dimmer 400 (FIG. 13). If the lamp interrupt is not detected to be timed out, the process at step 554 detects whether the indirect ophthalmoscope or the slit lamp interrupt has timed out. If this interrupt has timed out, the process next determines at step 556 whether the slit lamp is on. If the slit lamp is on, the process at step 558 triggers the slit lamp dimmer. If the slit lamp is not on, the process at step 560 triggers the indirect ophthalmoscope dimmer. The process then returns to the main routine 450.

Next, at process step 456, main routine 450 establishes a set of default parameters for status bits, output registers, etc.

Figure 16:
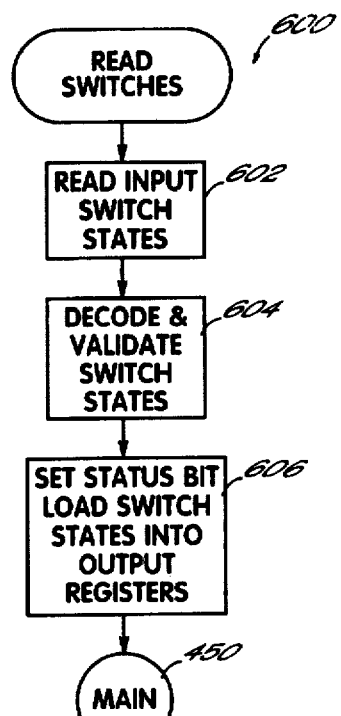
FIG. 16 is a flow chart showing the process steps of the read switches subroutine in the main routine of FIG. 15.

At process step 458, main routine 450 executes a read switches subroutine 600 as illustrated in FIG. 16. The first step 602 of the read switches subroutine 600 reads the states of the various input switches on the outputs 337 from optical buffers 336 (FIG. 13). The states of the various input switches are individually decoded and validated at process step 604 such that only predetermined acceptable input switch states are recognized. For example, the programming mode to be described below is activated by simultaneously actuating a combination of two switches, such as the raise and lower arrow switches 368 (FIG. 14).

At process step 606, the decoded and validated switch states are loaded into a command state output register within the group of registers 386. Appropriate status states are set in status registers included within the group of internal registers 386 as well. The status registers are used to track the current state of the control system operation as determined by, for example, the doctor. For example, status bits and registers may be used to indicate to the control whether the set up or programming mode has been activated, etc., as those of skill in the art will readily recognize.

Figure 17:
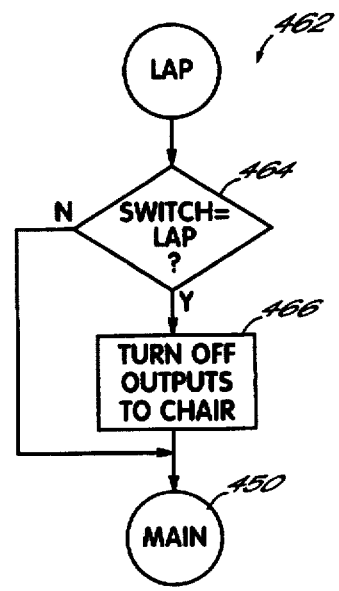
FIG. 17 is a flow chart showing the process steps of the lap subroutine in the main routine of FIG. 15.

Returning to FIG. 15, the main routine 450 then proceeds at step 460 to execute a "lap" subroutine 462 as illustrated in FIG. 17 to determine whether either one of the lap safety switches 282, 284 (FIGS. 9 and 10) have been actuated. Specifically, at process step 464 microprocessor 334 detects whether either one of these lap safety switches has been activated. If either one has been activated, all outputs to chair 18 (FIG. 1) are turned off at process step 466. Alternatively, the microprocessor 334 may direct the chair control to reverse the outputs to the chair 18 such that the chair is lowered away from table top 12 (FIG. 1). If neither of the lap safety switches is detected to be activated, the process returns to the main routine 450.

Figure 18:
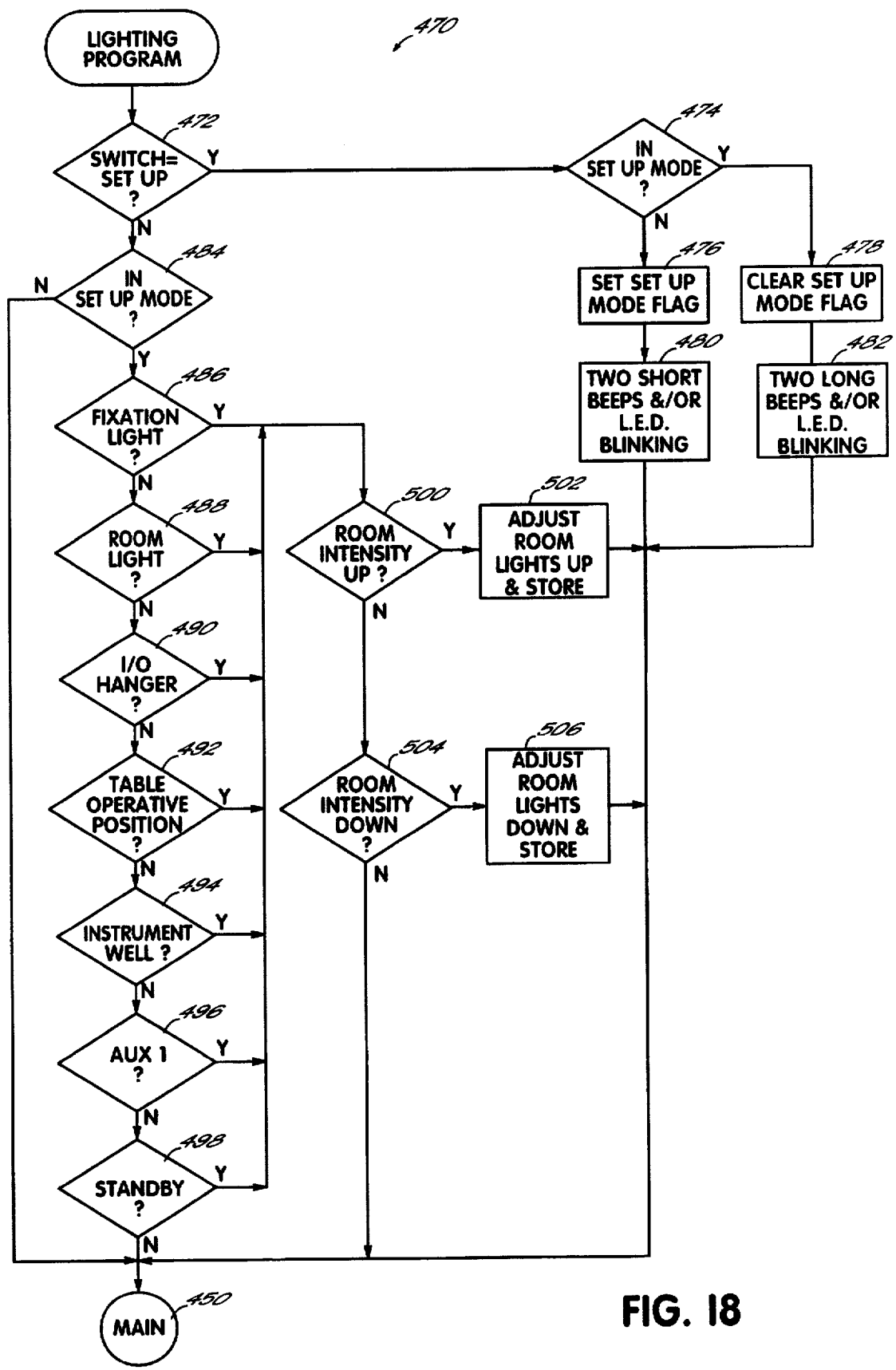
FIG. 18 is a flow chart showing the process steps of the lighting program subroutine in the main routine of FIG. 15.

Main routine 450 then proceeds at process step 468 to execute a programming mode subroutine as illustrated in FIG. 18. This programming mode is used only for the single zone option discussed above. First, at step 472, the lighting program subroutine 470 detects whether the current state of the switches which have been decoded and validated is representative of actuation of a set up switch. As previously mentioned, the "set up switch" may actually involve simultaneously actuating a combination of switches, such as switches 368 (FIG. 14). If activation of the set up switch is detected, the process at step 474 determines whether the set up mode is currently active. If the set up mode is currently inactive, the process at step 476 sets the set up mode flag. Otherwise, the process clears the set up mode flag at process step 478. Consequently, in steps 474, 476 and 478, the process successively activates and deactivates the set up mode in response to successive actuations of the set up switch. After setting the set up mode flag, the process at step 480 activates the tone generator 388 (FIG. 13) to produce two short beeps and/or causes suitable LEDs to activate indicating to the doctor that the programming or "set up" mode has been activated. If the set up mode flag is cleared, the process at step 482 activates the tone generator 388 to produce two long beeps and/or causes suitable LEDs to activate indicating that the programming or "set up" mode has been exited. Thereafter, the process returns to main routine 450.

If, at process step 472, the set up switch state is not detected, but the process at step 484 detects that the set up is activated, the process determines whether any of the programmable input switches to microprocessor 334 has been actuated. Representative switches are illustrated by process steps 486–498 in FIG. 18. These include any of the fixation light switches 378, 380, 382 (FIG. 14), room light switch 366 (FIG. 14), indirect ophthalmoscope hanger switch operated by hook 34 (FIG. 1), table operative position switch 162 (FIGS. 7 and 8), sensing circuits associated with instrument wells 30 (FIG. 1), "AUX1" switch 362 (FIG. 14) and standby switch 364 (FIG. 14). If any of these switches are detected as activated, the process at step 500 next determines whether the room lighting intensity is being adjusted upwardly by the doctor by actuation of switch 368 on main switch plate 340 (FIG. 14) and, if so, the process at step 502 adjusts the room lights through lighting control 302 to be more intense and stores this value in either volatile or nonvolatile memory for the particular switch or instrument which has been activated. If instead the room light intensity is being adjusted downwardly by operation of switch 368, the process detects this at process step 504 and accordingly adjusts the intensity of the room lights downward through control 302 and stores this for the particular switch or instrument. The process then returns to the main routine 450.

Figure 19:
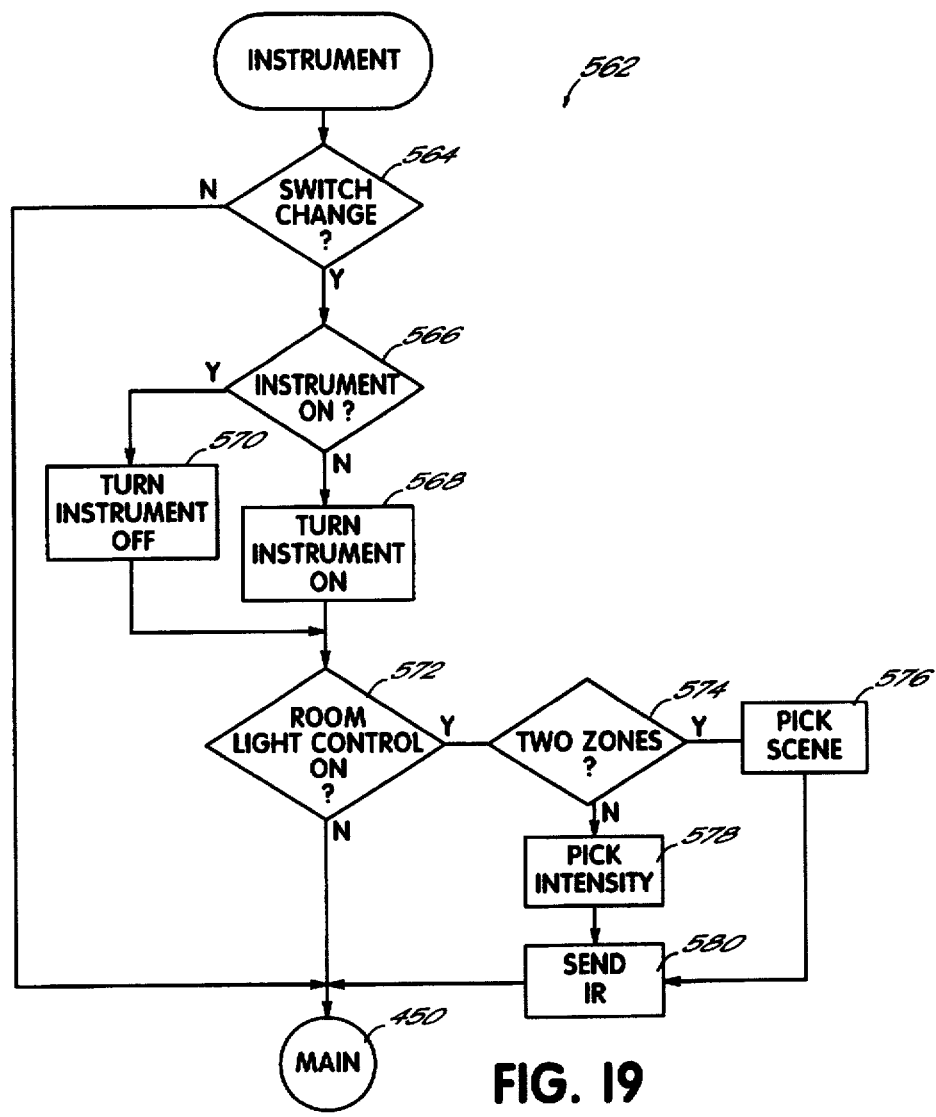
FIG. 19 is a flowchart showing the process steps of an instrument subroutine representing an illustrative subroutine of various instruments and switches shown in the main routine of FIG. 15.

Returning to FIG. 15, main routine 450 then proceeds through steps to determine active or inactive states for various switches, lights and instruments associated with the system. Each of process steps 508, 510, 512, 514, 516, 518, 520 is represented by the "instrument" subroutine 522 illustrated in FIG. 19. Specifically, at process step 564, the control detects whether one of the switches has changed its state from active to inactive or vice versa. If a change in switch state has been detected at step 564, the process at step 566 detects whether the instrument (or switch, light, etc.) is on. If no change in switch state is detected at step 564, the process returns to main routine 450. If the process detects that the instrument, switch, etc. , is off at step 566, the process turns it on at step 568. If it is detected to be on at step 566, the process turns the instrument, switch, etc., off at step 570. After either step 568 or 570, the process at step 572 determines whether the room light control has been enabled, such as by a dip switch 354 (FIG. 13). If the room light control has not been enabled, the process returns to main routine 450. If room light control has been enabled, the process at step 574 determines whether the system includes the two zone option, if so, the process at step 576 picks a "scene" corresponding to that particular instrument, switch, etc. If the two zone option is not detected, the process at step 578 picks the programmed intensity for that particular instrument, switch, etc. If the instrument, switch, etc., is turned off at step 570, then the process in step 576 or 578 may pick a default intensity or scene such as "full on" or the process may revert back to the intensity or scene which was active before the instrument, switch, etc., was turned on. After the process performs either step 576 or 578, the control sends the appropriate infrared data code at process step 580 and then returns to main routine 450. Process step 580 involves a separate subroutine as discussed below.

Figure 19A:
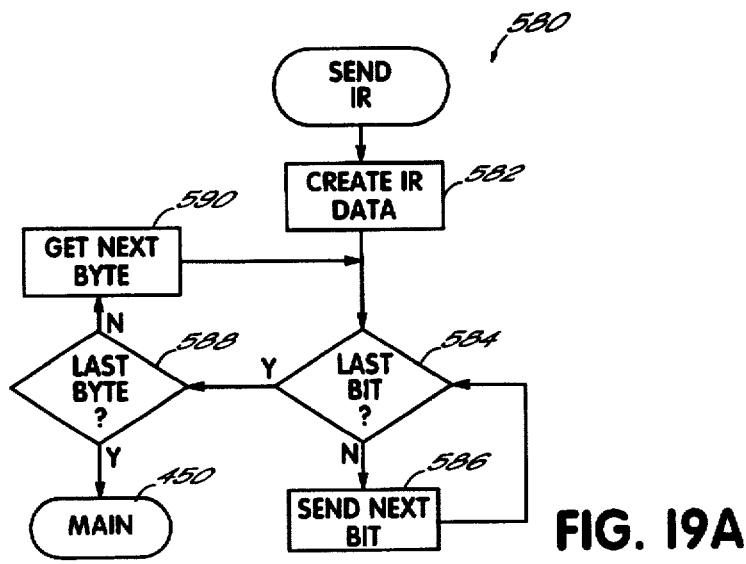
FIG. 19A is a flowchart illustrating a send IR subroutine of the instrument subroutine illustrated in FIG. 19.

The subroutine involved with sending the infrared code is illustrated in the flowchart of FIG. 19A. Specifically, at process step 582 of subroutine 580, the process creates infrared data for communicating with the lighting control 302 of control system 330. As is known to those of skill in the art, infrared codes may be created in a hex numbering system, for example, comprising 36 bits of information. Different 36 bit codes are sent representing different room lighting outputs in either the single zone or dual zone option. The system retrieves the infrared data in bytes and transmits this data in bits to the room lighting control 302. Therefore, at process step 584, the control determines whether the last bit of a given byte of the data string or code has been sent to lighting control 302. If it has not, the process at step 586 sends or transmits the next byte to the lighting control 302. If it detects that the last bit of a given has been sent to lighting control 302, the process at step 588 detects whether the last byte of the data string has been transmitted to the lighting control 302. If it has, the process returns to main routine 450. If it has not, the process retrieves the next byte at 590 and iterates through steps 584 and 586 until the entire 36 bit data string has been transmitted to lighting control 302 whereupon the subroutine will be exited and the process will return to main routine 450.

While a preferred embodiment of the present invention has been detailed herein, those of ordinary skill will recognize many modifications, substitutions of components and departures from this detailed description which nevertheless fall within the spirit and scope of the invention as set forth in the appended claims.

What is claimed is:

1. An ophthalmic instrument system for use in an examination room having a room lighting circuit, the system comprising:

an ophthalmic instrument support;

a plurality of input devices mounted on said ophthalmic instrument support; and, a programmable control including an output device and a dimming device connectable to the room lighting circuit, said programmable control being connected to said plurality of input devices and operative to allow different room lighting outputs to be selected by a user, stored by said control and sent by said control to said dimming device upon activation of each of said plurality of input devices to allow lighting intensity adjustment of said room lighting circuit by said dimming device.

2. The ophthalmic instrument system of claim 1 wherein said ophthalmic instrument support further includes an infrared transmitter operatively connected with said programmable control for transmitting said room lighting outputs to a receiver operatively connected to said dimming device.

3. The ophthalmic instrument system of claim 2 wherein said ophthalmic instrument support includes an instrument pole and said infrared transmitter is attached to said instrument pole.

4. The ophthalmic instrument system of claim 3 wherein said infrared transmitter is attached to said instrument pole in an adjustable manner.

5. The ophthalmic instrument system of claim 4 wherein said infrared transmitter includes a generally C-shaped portion which clips to said instrument pole in a manner allowing vertical movement along said pole and rotating adjustment about said pole.

6. The ophthalmic instrument system of claim 1 wherein said plurality of input devices include switches contained on a control panel physically connected with said ophthalmic instrument support.

7. The ophthalmic instrument system of claim 1 wherein one of said plurality of input devices is a sensing circuit connected to a recharging well for holding an ophthalmic instrument.

8. The ophthalmic instrument system of claim 1 wherein one of said plurality of input devices is a hanger switch connected to a hanger for holding, activating and deactivating an ophthalmic instrument.

9. The ophthalmic instrument system of claim 8 further comprising a toggling switch operatively connected with the hanger switch and operative to activate and deactivate a selectively programmed room lighting output in said control, wherein after activation of said toggling switch the selectively programmed room lighting output is sent to said dimming device upon activation of said hanger switch.

10. The ophthalmic instrument system of claim 1 wherein said programmable control includes a programming mode which may be entered by an operator, said programming mode allowing selectable input devices to be activated to select each of said plurality of input devices to be programmed with a desired room lighting output.

11. The ophthalmic instrument system of claim 10 wherein the selectable input devices are the same as said plurality of input devices.

12. The ophthalmic instrument system of claim 11 wherein a lighting intensity adjustment switch is provided in said control which may be actuated during said programming mode to adjust the room lighting output of each of said plurality of input devices.

13. An infrared transmitter comprising a body having a clip portion for clipping said body to a pole to allow vertical adjustment along said pole and at least one L.E.D. physically connected to said body for sending infrared signals to a receiver.

14. The infrared transmitter of claim 13 wherein said clip portion includes a generally C-shaped portion for engaging a cylindrical outer surface of said pole and allowing vertical sliding adjustment along said pole as well as rotating adjustment about said pole.

15. The infrared transmitter of claim 14 wherein a plurality of L.E.D. elements are spaced about an outer surface of said body.

16. An ophthalmic instrument system for use in an examination room having a room lighting circuit, the system comprising:

a plurality of ophthalmic instrument input devices; and, a programmable control including an output device and a dimming device connectable to the room lighting circuit, said programmable control being connected to said plurality of input devices and operative to allow different room lighting outputs to be selected by a user, stored by said control and sent by said control to said dimming device upon activation of each of said plurality of input devices to allow lighting intensity adjustment of said room lighting circuit by said dimming device.

* * * * *